United States Patent [19]

McNabb et al.

[11] Patent Number: 5,874,651
[45] Date of Patent: *Feb. 23, 1999

[54] RECOVERING PRODUCTS FROM A BY-PRODUCTS STREAM

[75] Inventors: Andrew J. McNabb; Rebecca E. Phillips, both of Lake Jackson, Tex.

[73] Assignee: BASF Corporation, Mt. Olive, N.J.

[*] Notice: This patent issued on a continued prosecution application filed under 37 CFR 1.53(d), and is subject to the twenty year patent term provisions of 35 U.S.C. 154(a)(2).

[21] Appl. No.: 771,545

[22] Filed: Dec. 23, 1996

[51] Int. Cl.⁶ .............................. C07C 27/26; C07C 35/08
[52] U.S. Cl. ............................................. 568/856; 568/822
[58] Field of Search ....................... 568/856, 822

[56] References Cited

U.S. PATENT DOCUMENTS

| | | | |
|---|---|---|---|
| 3,524,892 | 8/1970 | Horlenko et al. | 260/635 |
| 5,659,902 | 8/1997 | McNabb | 483/527 |

FOREIGN PATENT DOCUMENTS 2060548  6/1972  Germany .

*Primary Examiner*—Gary Geist
*Assistant Examiner*—Jafar Parsa

[57] ABSTRACT

A process for increasing the amount of isolatable products in a by-product stream generated in the production of 1,6 hexanediol includes combining the by-product stream with water to form a combination of the water and the by-product stream; and reacting the combination at a temperature between about 250° C. to about 400° C. at a pressure from about 1,000 psig to about 3,000 psig to form one or more reaction products.

9 Claims, 3 Drawing Sheets

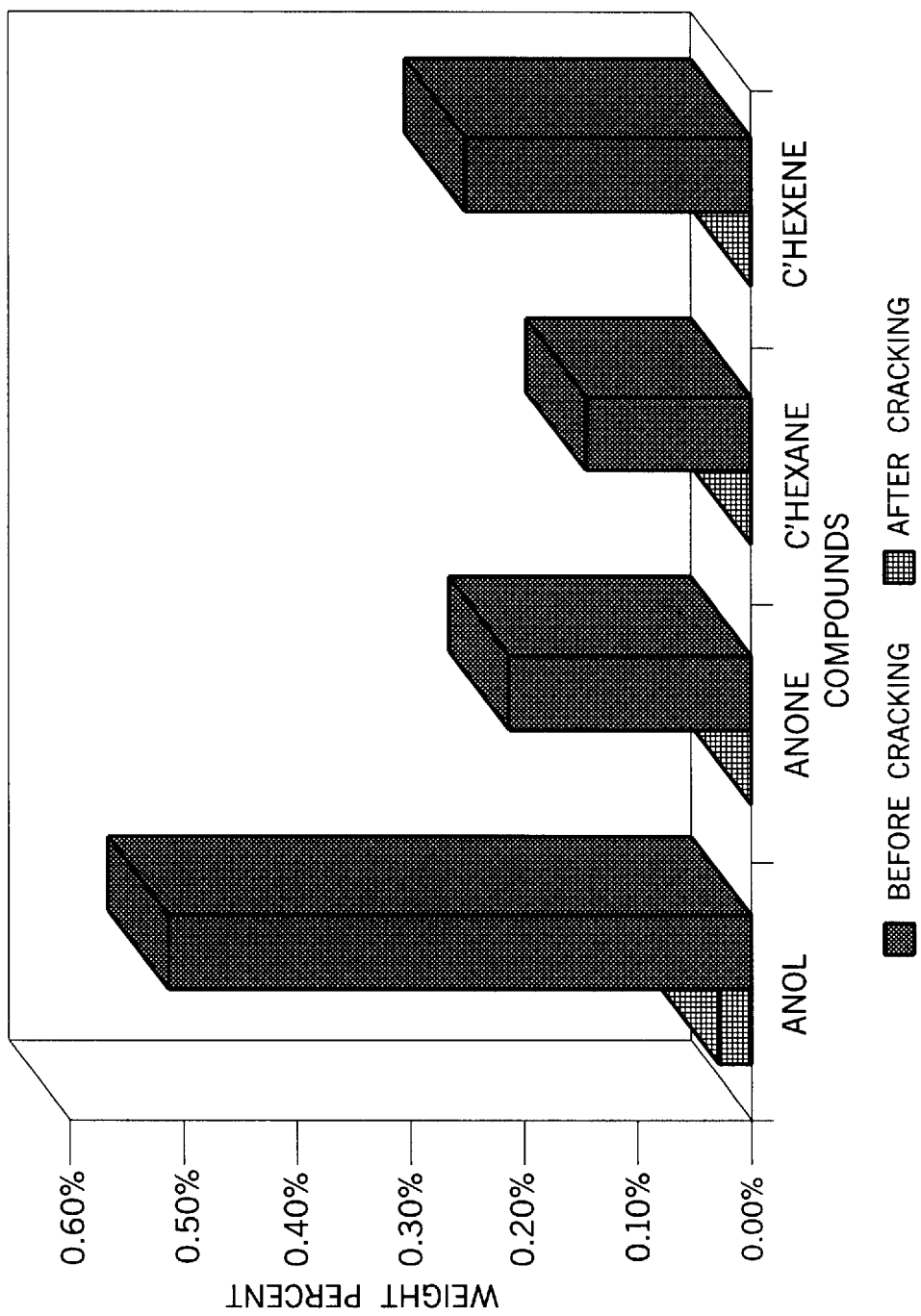

RECOVERING PRODUCTS FROM A BY-PRODUCTS STREAM

FIELD OF THE INVENTION

This invention relates generally to recovering products from a by-product stream. More specifically, this invention relates to recovering products from the by-product stream generated in the production of 1,6 hexanediol.

BACKGROUND OF THE INVENTION

Many chemical production processes produce by-product streams. These streams must be handled in some way. In some cases, these streams have historically been routed to waste and disposed of by, for example, deep welling or incineration. As a matter of efficiency, environmental stewardship, and process economics, it is usually desirable to minimize the size of the waste stream.

In a production scale distillation of 1,6, hexanediol ("HDO"), millions of pounds/year of by-product stream can be produced. Some production facilities store this stream in railcars (or other vessels) on the site until the streams can be handled properly. Not only do the vessels take up valuable space, railcars are often rented thereby adding to the cost of the product.

One of the fractions in the distillation of 1,6 hexanediol is referred to as "distillation heavies". It currently has little commercial value and is often used as fuel for steam generation. This stream represents a significant portion of the by-products from 1,6, hexanediol production. For example, in a typical 15M lb/yr hexanediol plant approximately 5.0 million pounds/year of distillation heavies might result. Reduction of the stream to useful products would, therefore, mean significant savings all around, i.e., environmentally, economically, efficiency, etc.

SUMMARY OF THE INVENTION

It has been surprisingly discovered that the by-product stream from 1,6 hexanediol production can be turned into useful products by a steam cracking process. Accordingly, the present invention is a process for increasing the amount of isolatable products in a by-product stream generated in the production of 1,6 hexanediol. The process involves the steps of combining the by-product stream with water to form a combination of water and by-product stream; and reacting the combination at a temperature between about 250° C. to about 400° C. at a pressure from about 1,000 psig to about 3,000 psig to form one or more reaction products.

It is an object of this invention to recover useful materials from the by-product stream in the production of 1,6 hexanediol.

It is another object of the present invention to recover additional 1,6 hexanediol from a by-product stream.

These and other objects and advantages which are achieved by the present invention can be readily discerned by those of ordinary skill in the art from the following description.

BRIEF DESCRIPTION OF THE DRAWINGS

FIG. 3 is a bar chart demonstrating the effectiveness of the present invention to produce several products.

DESCRIPTION OF THE PREFERRED EMBODIMENTS

Figure 1:
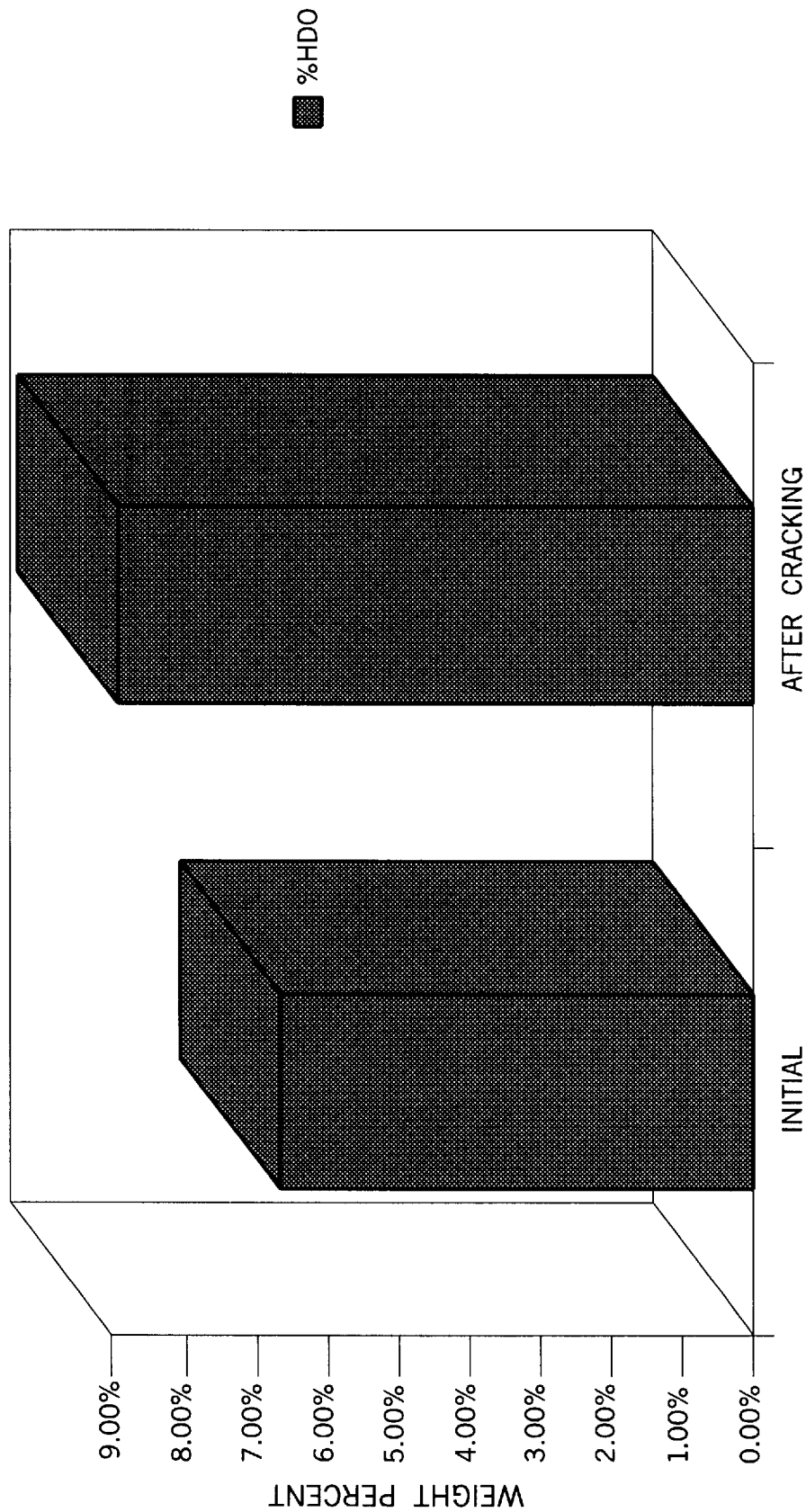
FIG. 1 is bar chart demonstrating the production of 1,6 hexanediol by the process of the present invention.

To promote an understanding of the principles of the present invention, descriptions of specific embodiments of the invention follow and specific language is used to describe them. It will nevertheless be understood that no limitation of the scope of the invention is intended by the use of specific language. Alterations, further modifications and such further applications of the principles of the invention discussed are contemplated as would normally occur to one ordinarily skilled in the art to which the invention pertains.

Distillation heavies from the production of 1,6 hexanediol typically are composed of 1,6 hexanediol (about 3 to about 10 wt. %), 6,6' dihydroxydihexyl ether (about 3 to about 10 wt. %), cyclic trimer (about 11 to about 14 wt. %), water (less than about 1 wt. %) and the rest is other diols, esters and ethers. It has been surprisingly discovered that the content of isolatable useful products, i.e., those products that can be isolated, in these distillation heavies can be increased by a steam cracking process.

The present invention is a process for increasing the useful products in a by-product stream by combining the by-product stream with water to form a combination of water and the by-product stream. The combined water and by-product stream are reacted at a temperature between about 250° C. and about 400° C. and a pressure from about 1,000 psig to about 3,000 psig to form one or more reaction products. Preferably, the amount of water added will be sufficient to bring the water content to between about 0.1% and about 20% by wt. of the combination. The time for the reaction is preferably between about 0.1 and about 6 hours.

The process of the present invention can further include the steps of separating the reaction products into fractions. The separation can be accomplished by many methods known in the art. Preferably, the separation is by vacuum distillation. The separation step may result in two or more fractions. The product may be recovered individually or a single targeted product may recovered depending on which products are desired for further use or sale. Typically, three fractions result from the separation step. These may be characterized as the heavy fraction (i.e., having a boiling point higher than that of HDO); 1,6 hexanediol, and the light fraction (i.e., having a boiling point lower than that of HDO).

The light fraction may contain cyclohexane, cyclohexene, cyclohexanone and cyclohexanol. These chemicals may be recovered by conventional techniques, e.g., distillation, used as fuel for heat recovery, etc.

By the process of the present invention, 1,6 hexanediol is produced at a rate of about 2 lbs. for every 100 lbs. of typical distillation heavies. Of course, it will be understood that this increase is a function of the amount of esters and other HDO-containing materials in the heavies and should not be dependent on the amount of HDO present in the heavies. That is, if pure HDO is added to the distillation heavies such that it contains 9.6% HDO instead of 6.6% HDO, the HDO content should still increase by 2.3 lb/100 lb. It will be understood by those ordinarily skilled in the art, however, that the increase in HDO will depend to an extent on the amount of esters and other HDO containing compounds (i.e., the amount of HDO available in the heavies).

Therefore, the amount of HDO produced per 100 lbs. will vary according to the nature of the distillation heavies used as a starting material. Exemplary amounts of products achieved with the present invention are as follows (in % by weight):

Cyclohexane, (%) 0.06–0.60

Cyclohexanone, (%) 0.10–1.0

Cyclohexanol, (%) 0.20–2.0; and 1,6 Hexanediol, (%) 1.0–10.0

It is preferred that the reaction product is cooled to ambient temperature and the pressure reduced to ambient pressure prior to the separating. The cooling may be accomplished through common cooling means or by allowing the mixture to sit long enough to reach ambient temperature.

The invention will now be described by referring to the following detailed example. This example is set forth by way of illustration and is not intended to be limiting in scope. All percentages given in the example or elsewhere are by weight unless indicated otherwise.

EXAMPLE

The concentration of materials in this example is measured using gas chromatography. The GC is a Hewlett Packard 5890 Series II. The column is a DB Wax J+W column, 30M×0.25 mm, 0.25μ film thickness, except that a CP-Sil 8CB 25m column is used for cyclohexanone quantification. Helium is the carrier. The temperature program is 180° C./12 min ramped to 240° C./2 min at 20° C./min. The flame ionization detector operates at 300° C. Samples are diluted in methanol.

Figure 2:
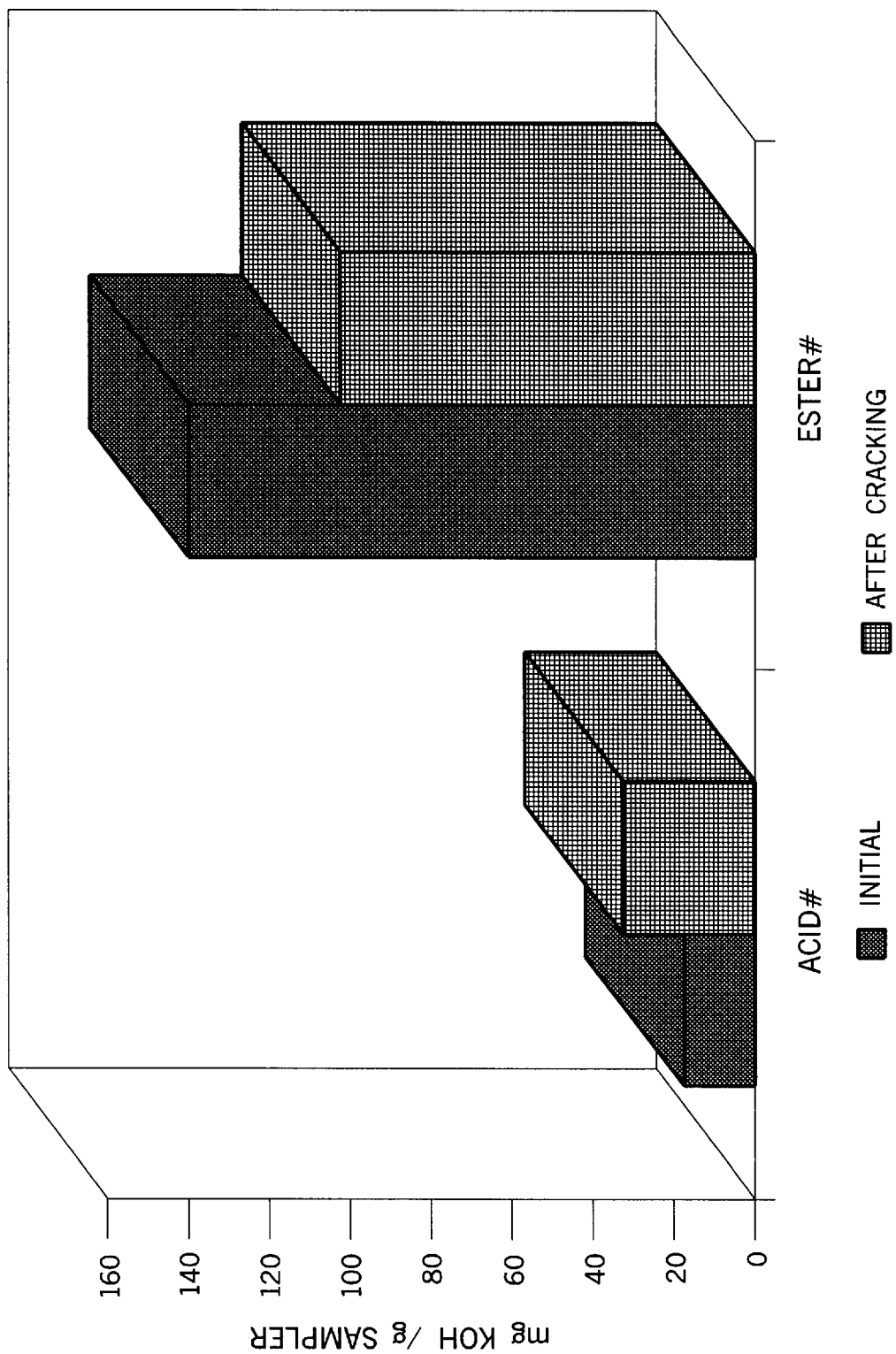
FIG. 2 is bar chart demonstrating the increase in the acid number and decrease in the ester number of a by-product stream by the process of the present invention.

The distillation heavies from the production of 1,6 hexanediol are analyzed for 1,6, hexanediol ("HDO"), acid number, ester number, cyclohexanone and cyclohexanol content. Approximately 300 grams of heavies from the distillation of 1,6 hexanediol and 30 grams of water are added to a Parr mini reactor cylinder. A nitrogen purge is used. The residence time in the reactor is 60 minutes. The pressure is approximately 1600 psi. The temperature is about 326° C. After reaction, the reactor contents are analyzed for HDO and other products. The results are presented in the Table and illustrated graphically in the FIGs. There is a 35% increase of HDO. The acid number increased 96% and the ester number decreased 28% (see FIG. 2). This signifies that that some of the esters are cracked into 1,6 hexanediol and acids. Other compounds that are produced include 0.5% cyclohexanol, 0.2% cyclohexanone, 0.2% cyclohexane and 0.3% cyclohexene (see FIG. 3).

TABLE 1

|  | Before Cracking | After Cracking |
| --- | --- | --- |
| HDO(%) | 6.62 | 8.94 |
| Acid # | 16.95 | 33.18 |
| Ester # | 141.55 | 102.14 |
| Cyclohexanol(%) | 0.03 | 0.52 |
| Cyclohexanone(%) | 0.00 | 0.21 |
| Cyclohexane(%) | 0.00 | 0.15 |
| Cyclohexene(%) | 0.00 | 0.25 |

What is claimed is:

1. A process for increasing the amount of isolatable products in a by-product stream generated in the production of 1,6 hexanediol comprising the steps of:
   (a) isolating a heavy by-product stream comprising 1,6 hexanediol cyclic trimer, esters and ethers from distillation of 1,6 hexanediol;
   (b) combining the heavy by-product stream with water to form a combination of water and by-product stream; and
   (c) reacting the combination at a temperature between about 250° C. and about 400° C. at a pressure from about 1,000 psig to about 3,000 psig to hydrolyze the heavy by-product stream to form one or more reaction products.

2. The process of claim 1 wherein said combining is with water sufficient to provide from about 0.1% to about 20% by weight of water in the combination.

3. The process of claim 1 wherein said reacting is for between about 0.1 to about 6 hours.

4. The process of claim 1 further comprising the step of:
   (d) separating the reaction product into fractions.

5. The process of claim 4 further comprising the step of
   (e) cooling the reaction product and reducing the pressure to ambient atmospheric pressure and temperature prior to said separating.

6. The process of claim 4 wherein said separating is by vacuum distillation.

7. The process of claim 4 wherein said fractions are separated out of the reaction product.

8. The process of claim 7 wherein there are at least three fractions comprising a heavy fraction, 1,6 hexanediol and a light fraction.

9. The process of claim 8 wherein the 1,6 hexanediol fraction is about 9% by weight of the reaction product.

* * * * *